United States Patent
Chawki

(10) Patent No.: US 7,618,400 B2
(45) Date of Patent: Nov. 17, 2009

(54) DRESSING FOR SECURING AND PROTECTING A NEEDLE

(75) Inventor: Mokhtar Chawki, Le Vésinet (FR)

(73) Assignee: Nephrokit SARL, Le Vesinet (FR)

( * ) Notice: Subject to any disclaimer, the term of this patent is extended or adjusted under 35 U.S.C. 154(b) by 0 days.

(21) Appl. No.: 11/813,956

(22) PCT Filed: Jan. 26, 2005

(86) PCT No.: PCT/EP2005/001523

§ 371 (c)(1), (2), (4) Date: Aug. 9, 2007

(87) PCT Pub. No.: WO2006/074700

PCT Pub. Date: Jul. 20, 2006

(65) Prior Publication Data

US 2008/0045905 A1 Feb. 21, 2008

(30) Foreign Application Priority Data

Jan. 14, 2005 (FR) .................................. 05 00415

(51) Int. Cl.
A61M 5/32 (2006.01)
(52) U.S. Cl. .................. 604/174; 604/180; 604/192
(58) Field of Classification Search ................ 604/263, 604/174, 192–198, 110, 180
See application file for complete search history.

(56) References Cited

U.S. PATENT DOCUMENTS

| 3,885,560 | A | * | 5/1975 | Baldwin | 604/177 |
|---|---|---|---|---|---|
| 3,900,026 | A | * | 8/1975 | Wagner | 128/888 |
| 4,941,882 | A | * | 7/1990 | Ward et al. | 604/180 |
| 5,968,000 | A |   | 10/1999 | Harrison et al. |   |
| 6,273,873 | B1 | * | 8/2001 | Fleischer | 604/174 |
| 7,387,616 | B2 | * | 6/2008 | Li | 604/198 |
| 2002/0161332 | A1 |   | 10/2002 | Ramey |   |

FOREIGN PATENT DOCUMENTS

| DE | 20210493 | 11/2003 |
|---|---|---|
| EP | 0284219 | 9/1988 |
| JP | 2004147855 | 5/2004 |
| WO | WO 02083206 | 10/2002 |

OTHER PUBLICATIONS

International Search Report for PCT/EP2005/001523.

* cited by examiner

*Primary Examiner*—Kevin C Sirmons
*Assistant Examiner*—Imani Hayman
(74) *Attorney, Agent, or Firm*—Scott E. Kamholz; Peter K. Sollins; Foley Hoag, LLP

(57) ABSTRACT

A device for securing and protecting a needle, the device comprising a first portion (3) and a second portion (5), each provided with an adhesive face covered in a detachable anti-adhesive sheet, the first portion (3) being for securing to the skin, in register with the penetration site selected for the needle, and the second portion (5) being for overlying the penetration site of the needle, the device being made of a flexible material and having a longitudinal slot (2) for passing the needle and a transverse bearing zone for the needle, with only one of the faces of the first portion (3) being adhesive, the second portion (5) being suitable and configured to be secured to the skin while overlying the needle penetration site and without being stuck to the first portion (3).

24 Claims, 3 Drawing Sheets

DRESSING FOR SECURING AND PROTECTING A NEEDLE

CROSS-REFERENCE TO RELATED APPLICATIONS

This application is the National Stage of International application Ser. No. PCT/EP2005/001523, filed Jan. 26, 2005, hereby incorporated herein by reference, which claims the benefit of French application Ser. No. 05/00415, filed Jan. 14, 2005, also hereby incorporated herein by reference.

The invention relates to the medical or veterinary field, and concerns means for holding needles and more particularly, but not exclusively, needles having wings.

The invention also relates to a device for protecting the entry site of a needle.

The invention relates in particular to medical or veterinary use of intravenous catheters.

The invention is of particular interest in the field of hemodialysis, or that of performing perfusions using needles/catheters or short intravenous devices of the Cathlon® type (PTFE cannulas).

The invention relates in particular to a device for fastening winged needles to the vein puncture site during a venous or arteriovenous perfusion, in particular for arteriovenous fistula (AVF) due to hemodialysis.

It is common practice to withdraw or inject fluids (electrolytes, anesthetic isotonic glucose serum, . . . ), or to administer medication to a patient or an animal via a tube secured to a needle or to a catheter.

The needle or catheter needs to be inserted manually and in a precise location, e.g. intravenously, intramuscularly, or subcutaneously.

Winged needles are used for transfusions, in particular for taking a blood sample. Such needles are so-called because they are provided with a manual pinch zone in the form of butterfly wings. Pressing the wings against each other makes the needle easy to grasp and facilitates insertion thereof under the skin. Once the needle has been put into place, the wings are conventionally folded down onto the skin and an adhesive tape is placed over the wings and on the skin in order to prevent the needle being extracted.

Examples of winged needles are to be found in the U.S. patents granted under the following numbers: U.S. Pat. Nos. 2,725,058, 3,064,648, 3,640,275, 4,194,504, 4,300,553, 4,627,842, 5,108,376, 5,149,328, and 6,270,480.

When the needle is inserted in a blood vessel, even small movements of the needle can run the risk of phlebitis or hematoma, with the needle passing right through the vessel.

Conventionally, needles are held in place by using a large number of pieces of adhesive tape. The quality of needle retention thus depends particularly on the care of the person putting the adhesive tape into place. Such adhesive tapes are uncomfortable and can lead to problems with the skin.

The use of conventional adhesive tapes does not serve to avoid the risks of a needle being extracted accidentally, e.g. when intravenous perfusions are performed on children, since they find it difficult keep still for long periods of time.

Uncontrolled movements of people suffering from neurodegenerative diseases (Parkinson's, Alzheimer's) can also lead to needles being pulled out, with a loss of substances essential for maintaining the patient's life or the patient's physical or mental equilibrium, e.g. blood, curative substances, nutritional elements, palliative care substances.

The use of conventional adhesive tapes usually hides the tubing at least in part, which means that it can sometimes be difficult to verify visually that fluid injection or drainage is taking place properly.

Periodically removing adhesive tapes in order to perform such verification is tedious, disagreeable to the patient, and increases the danger of the needle being moved accidentally.

Such adhesive tapes frequently stick to the gloves of an operator, and that leads to a danger of being pricked, as is well-known and feared by nurses. The spread of AIDS, of various kinds of hepatitis, and of other contagious diseases via blood makes this risk all the more dangerous. Unfortunately, conventional adhesives adhere to the wings of needles and also stick to the fingers of gloves, thereby causing traction to be applied to the needle, whose tip can accidentally prick the operator.

It is sometimes desirable to withdraw the needle quickly, but that is not easy when the needle is secured by a multitude of adhesive tapes placed in all directions.

When the patient's skin is wet, due to fluid flow or to sweating, certain adhesive tapes can become unstuck from the skin, so that the needle is no longer properly secured.

It is estimated that about 80% of hospital patients are subjected to treatment administered by an intravenous catheter. Although peripheral intravenous catheters are less subject to infection than deep intravenous catheters and central venous catheters, it is not unusual for peripheral venous catheters to be infected with staphylococcus. It is assumed that movements of needles encourage such infections.

For some patients, peripheral catheters are in chronic use. This applies in particular to patients suffering acute or chronic renal insufficiency and under treatment by hemodialysis or extra-renal purification.

Hemodialysis assists in maintaining normal chemical equilibria in the blood, in particular in terms of potassium, sodium, and chlorine, and also serves to extract toxins.

A hemodialysis session lasts for about four hours, and needs to be performed three times a week.

Vascular access in patients undergoing hemodialysis is of great importance, and such vascular access must make it possible to use high flow rates so as to make it possible to reduce the duration of a dialysis session. An ordinary vein does not provide an adequate flow rate.

Three types of vascular access are predominant in hemodialysis: arteriovenous fistulas, arteriovenous prostheses or grafts, and central venous catheters (CVC).

AVFs are anastomoses that are surgically created to connect an artery and a vein of the patient, commonly in the forearm, or the arm, usually between a radial or humeral artery and the corresponding vein. The anastomosis serves to increase the blood flow rate within said vein. AVFs present very few complications compared with other vascular accesses, but they require a period of several weeks to several months to mature, during which time the diameter of the AVF increases. Creating an AVF changes the appearance of the patient's forearm considerably, by creating aneurysm zones. That is why numerous rigid needle-holding devices known in the prior art cannot be used for holding dialysis needles on an AVF.

The needles used for puncturing AVFs are of large caliber, having an inside diameter lying typically in the range 1.6 millimeters (mm) to 2 mm. The needle taking blood from the patient to the dialysis apparatus is referred to as an "artery", and the needle returning the blood to the patient is referred to as a "vein".

During a hemodialysis session for a patient, several incidents or accidents need to be avoided.

A poorly secured needle represents a real danger for the patient, given the high flow rates at which an AVF operates. Any bleeding from the puncture point can be fatal to the patient. In addition, during hemodialysis, an anticoagulant is used to limit the risk of the lumens of the catheters becoming blocked by thromboses. Because high blood rates and an anticoagulant are in use, the risks associated with dialysis needles accidentally being pulled out are very great.

It is common to observe local bleeding between the cutaneous wall and the point of insertion of the needle, with this being a factor contributing to infectious contamination through the puncture wall. To avoid this hazard, retention devices must impose permanent penetration pressure on the needle during dialysis.

During puncturing or during a dialysis session, a needle may transfix the wall of the vessel. In other words, the needle may pass through the wall of the vessel and lead to hematoma. When this happens with the venous needle, the blood is reinjected under pressure during the dialysis session and leads to a voluminous hematoma. More rarely, the needle penetrates an underlying artery, thereby leading to a deep hematoma. An aneurysm can develop on the artery at a subsequent date. Such an aneurysm requires surgical treatment.

During dialysis, a hematoma may occur when the needle is secured after it has partially skewered the wall of the vessel. The needle can then become transfixed during jerky or involuntary movements of the patient. It is then necessary to stop the dialysis session prematurely, which means that the quality of extra-renal purification will be poor.

Accidental needle extraction while blood is circulating outside the body constitutes a severe accident. It is in particular very severe when the needle is the vein needle. Such an accident can lead to the death of the patient by iatrogenic hemorrhage. In the absence of a specific alarm on the circulation outside the body, the blood pump continues to operate and empties the patient of blood.

Such an accident is liable to occur, for example, with patients who do not keep still, or who are depressive, epileptic, or suffering from chorea, a neurodegenerative disease such as Parkinson's, Parkinson's syndrome, or who suffer from convulsions for various reasons.

Inappropriate disconnection of the artery needle leads to bleeding at the puncture point and runs the risk of gaseous embolism. Although rare because of the presence of an air detector in modern dialysis apparatuses, this risk nevertheless remains real when blood flow rates are high, because of the latency in the response of the safety clamp.

Simultaneous disconnection of both needles has two consequences for the patient: loss of 250 cubic centimeters (cc) of blood, and bleeding at the puncture points. Such bleeding requires the dialysis session to be interrupted and compression prior to possible restarting of a new session.

A prosthesis or graft is put into place surgically, and also leads to an arteriovenous connection provided by a duct of biocompatible polymer material. The dialysis needles are inserted into the synthetic duct which requires considerable manual force. Grafts require no or little maturing time but they lead to risks of stenosis and thrombosis that are greater than the corresponding risks for AVFs.

The risks associated with disconnection of dialysis needles implanted in an AVF are substantially the same as those associated with disconnection of dialysis needles implanted in a graft.

Winged needles for hemodialysis are traditionally secured with a plurality of adhesive tapes, at least one of which is stuck in a V-shape or necktie configuration causing the adhesive to pass under the tubing and then over the wings.

Conventional devices for securing perfusion needles or catheters cannot be used with most patients under dialysis for the following reasons.

Firstly, some prior art devices are rigid. Unfortunately AVFs, which are the first choice and most widespread form of vascular access, lead to the appearance of aneurysm zones, with the skin being greatly deformed in the vicinity of an AVF. The use of rigid retention devices leads to repeated irritation of the skin, encouraging excoriation, which is particularly likely to lead to bacterial contamination. In addition, fistulas can be kept active for very many years, and the skin of certain patients undergoing dialysis is not very flexible, thin, and fragile because of age.

Secondly, certain prior art devices for retaining needles includes straps. Such straps are completely unacceptable for patients having an AVF because of the risk of a tourniquet effect that can lead to ischemia.

Thirdly, a large number of such prior art devices for retaining needles are large in size. However, AVFs are usually short, such that the artery and vein needles need to be put into place close to each other.

After studying the problems set out above in depth, the present inventor has devised a device providing numerous advantages and enabling the above-mentioned difficulties to be greatly attenuated.

In complete opposition to the conventional means of the prior art, and in particular those described in U.S. Pat. Nos. 4,863,432, 4,534,762, 4,490,141, and 5,087,248, the present inventor proposes a device in which the needle, in particular a winged needle, is not stuck to the skin, and is not in contact with any adhesive tape, but nevertheless remains firmly in position in spite of those features which are a priori counterintuitive.

Thus, in a first aspect, the invention provides a device for holding and protecting a needle, the device comprising a first portion and a second portion, each provided with an adhesive face covered in a detachable anti-adhesive sheet, the first portion being for securing to the skin, in register with the penetration site selected for the needle, and the second portion being for covering the penetration site of the needle, the device being characterized in that it is made of a flexible material and in that it has a longitudinal slot for passing the needle and a transverse bearing zone for the needle on either side of the slot, only one of the faces of the first portion being adhesive, the second portion being suitable and configured to be secured to the skin when overlying the penetration site of the needle, without being stuck to the first portion.

Advantageously, the device is made of an elastic material, in particular a material that is elastic in the longitudinal and transverse directions. The device can be secured on surfaces that are very deformed, in particular on the aneurysm zones of AVFs.

Advantageously, the device includes a window of transparent or translucent material so as to enable the needle penetration point to be seen, without any need to remove the dressing.

In an advantageous embodiment, the first and second portions constitute a single strip of flexible material hinged about a transverse fold zone, the longitudinal slot extending on either side of the fold zone, the maximum width of the slot as measured substantially along the fold direction being defined in said fold zone.

In an embodiment, the second portion is of shape substantially identical to the first portion, e.g. oval, square, or rectangular, and is provided with lateral adhesive lugs, in particular it includes two transverse adhesive lateral lugs situated substantially in line with the fold zone. In a particular embodiment, the second portion is of dimensions that are greater than those of the first portion and is provided with an adhesive peripheral margin.

In certain embodiments, in order to ensure that the needle has an angle of incidence that is as constant as possible, the device comprises a semirigid material on either side of the longitudinal slot, the thickness and the shape of the material enabling an angle of incidence for the needle to be substantially conserved.

In a second aspect, the invention relates to a perfusion kit comprising a device as presented above and a needle passed through the protection device and temporarily secured thereto. The kit is ready for use and can be sold flat.

Advantageously, in the kit, the needle is a winged needle and is secured to the device in temporary manner, e.g. by snap-fastening.

Other objects and advantages of the invention appear from the following description of presently-preferred embodiments, which description is given with reference to the accompanying drawings, in which.

In the description below, the dressing 1 for securing and protecting the needle and shown in the accompanying figures is referred to for short as a "dressing".

The dressing 1 as shown is generally rectangular in shape with rounded corners or it is oval in shape, and it has a longitudinal plane of symmetry P1.

The dressing 1 includes a longitudinal slot 2 for passing a needle. The slot 2 is meniscus-shaped being broader halfway along its length than at its two opposite ends.

Figure 2:
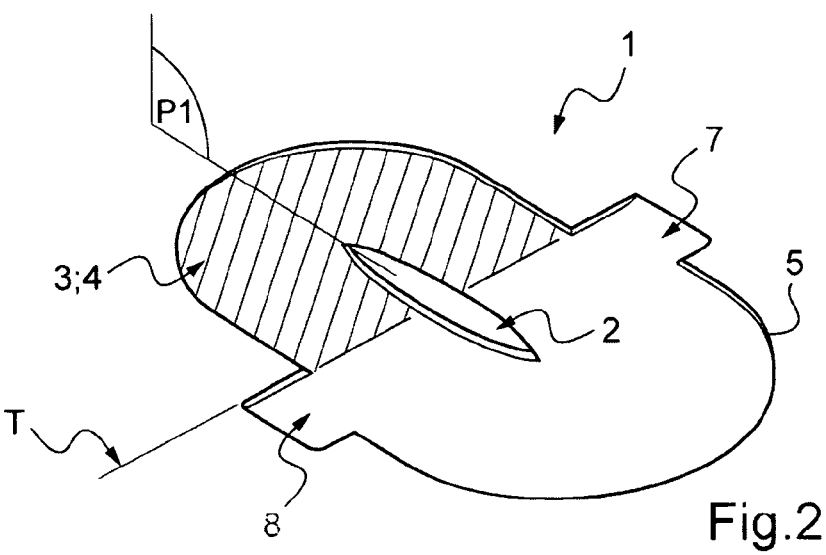
FIG. 2 is a view showing the FIG. 1 dressing, showing the bottom face thereof, the dressing being ready for putting into place.

In a first portion 3, referred to as a "front" portion, the dressing 1 is adhesive on its first face referred to as its "bottom" face. This adhesive bottom front face 4 is represented by shading in FIG. 2.

In its second portion 5, referred to as its "rear" portion, and on its second face, referred to as its "top" face, the dressing 1 is provided with an adhesive margin 6.

Figure 1:
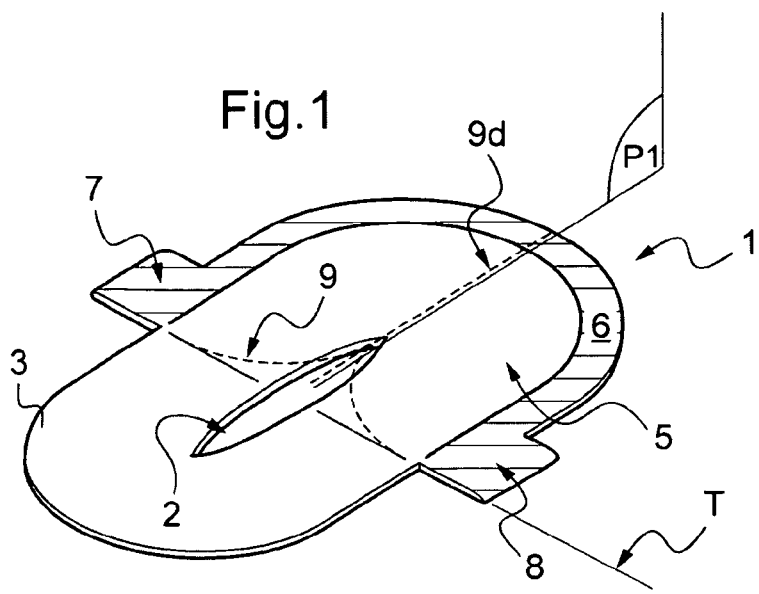
FIG. 1 is a perspective view showing the top face of a dressing for securing and protecting a needle, the dressing being shown flat.

The adhesive margin 6 of the top rear face of the dressing 1 is represented by shading in FIG. 1.

The dressing 1 is provided with two transverse side lugs 7 and 8 which are adhesive on the top face of the dressing that can be seen in FIG. 1.

Peel-off films are placed over the adhesive zones of the dressing prior to use. One of these peel-off films 9 is shown partially withdrawn in FIG. 1.

By using release lines 9d, removing these peel-off films over precise planes makes it easier to secure the dressing while avoiding any risk of sticking to the gloves of the operator or of wrinkling. A longitudinal release line 9d is shown in FIG. 1.

Figure 5:
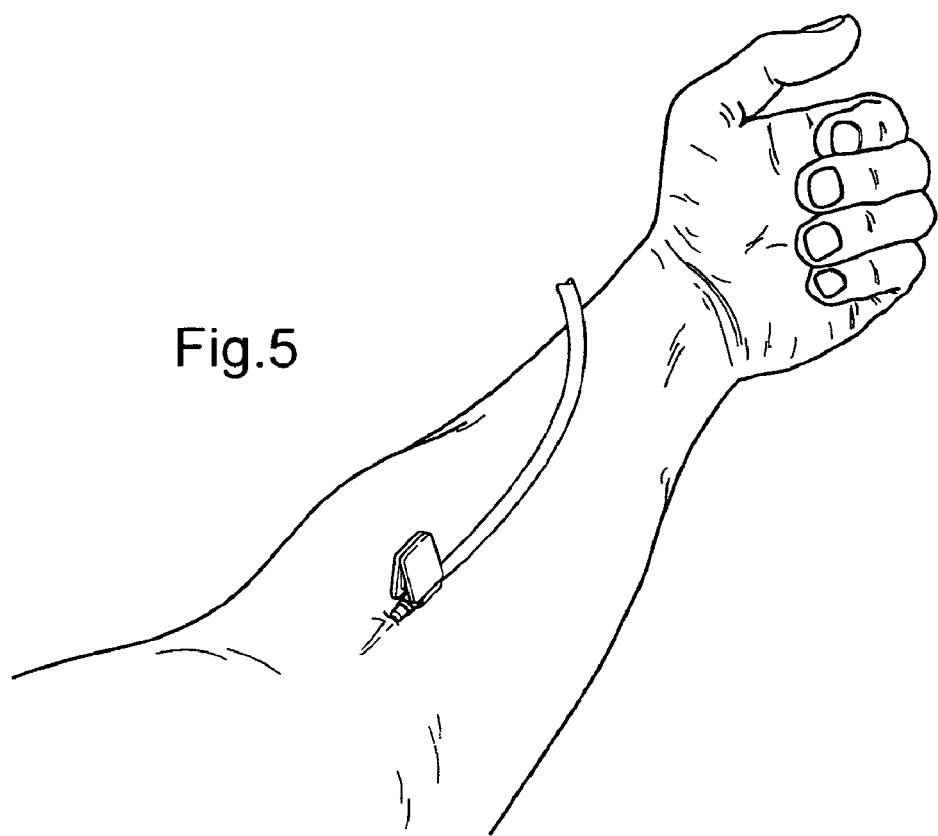
FIG. 5 is a view showing the needle of FIGS. 3 and 4 being inserted into the forearm of a patient.

The dressing is advantageously used as follows when a winged needle is to be secured and protected, the winged needle being inserted in conventional manner as shown in FIG. 5 in the desired position, e.g. in a blood vessel or an AVF.

Firstly, the operator removes the peel-off film covering the front bottom face 4 of the dressing.

Thereafter, the front bottom face 4 is pressed against the skin of the patient or the animal, so that the slot 2 is in register with the needle entry site, the operator then passing the needle 10 through the slot 2.

Figure 6:
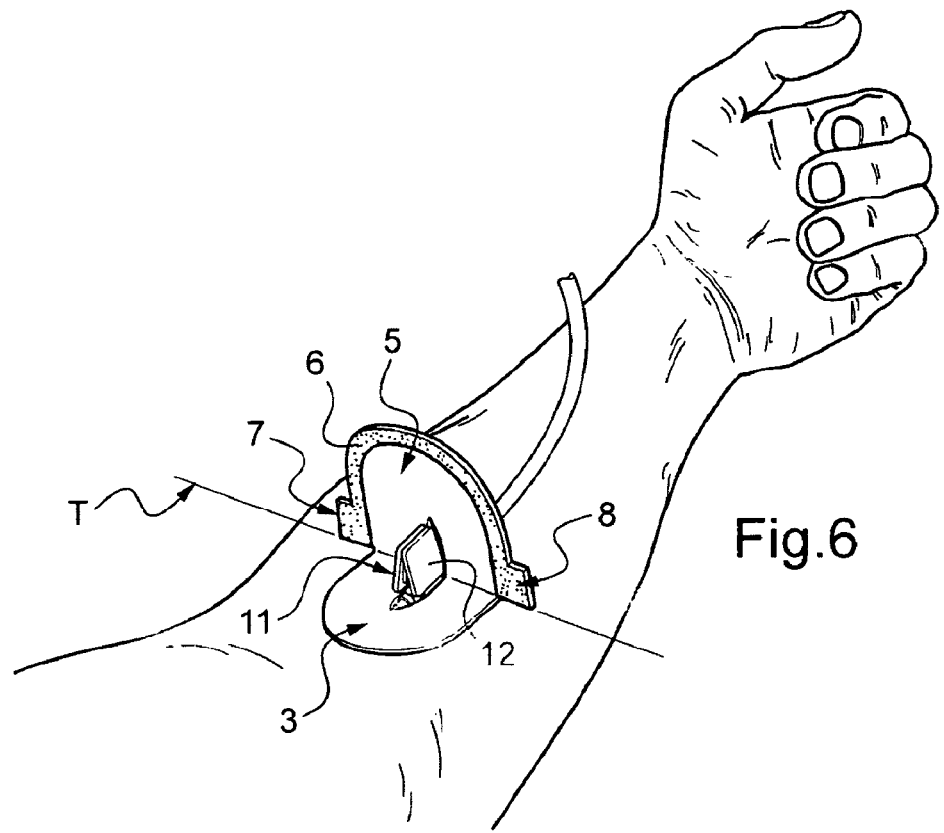
FIG. 6 is a view showing a dressing constituting an embodiment of the invention being put into place, with the wings of the needle being in the folded-up position.
Figure 7:
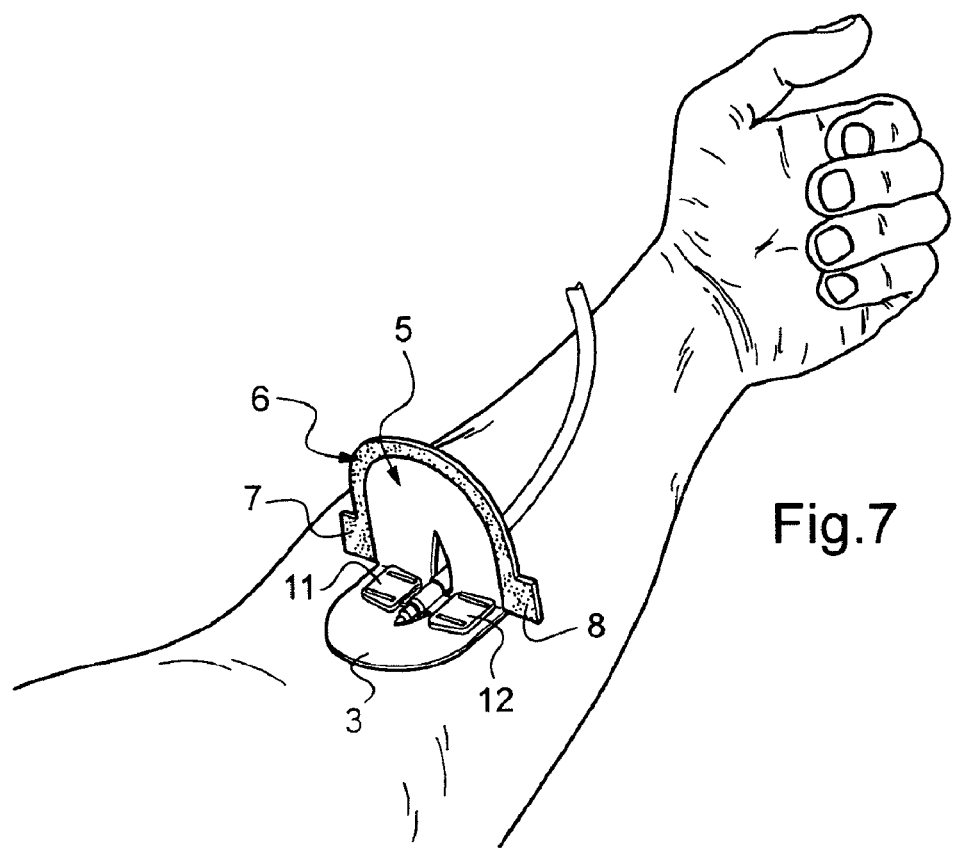
FIG. 7 is a view analogous to FIG. 6, with the wings of the needle being in a folded-down position, for reasons of clarity, the hands of the operator (nurse, radiologist) are not shown.

It should be observed that the operator can use the winged needle in conventional manner, folding the wings up against each other to improve grip and pointing of the needle 10, with the wings 11, 12 being released once the needle 10 is in place, so that the wings 11, 12 then fold down against the front face of the dressing 1 on either side of the slot 2, as shown in FIG. 6.

Figure 3:
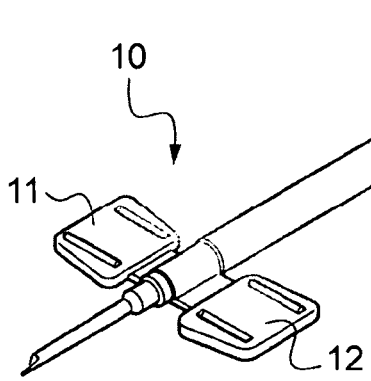
FIG. 3 is a perspective view of a winged needle.
Figure 4:
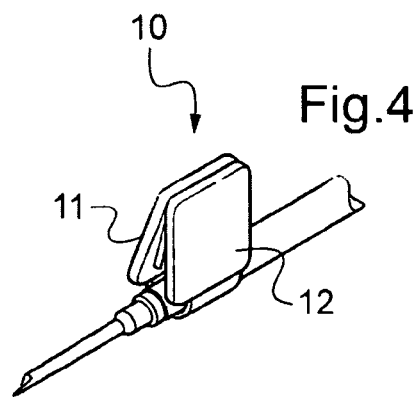
FIG. 4 is a perspective view of the FIG. 3 needle with its wings folded up against each other.

The width of the slot 2 is significantly smaller than the width of the wings 11, 12 when they are in the folded-down position as shown in FIG. 3.

The invention does not require the operator to change habitual practice concerning inserting the needle through the skin, which is of great comfort to operators. Nor is it difficult for an operator to pass the winged needle through the slot 2, since the dressing 1 is made of flexible material such as a coated fabric or an equivalent, with the width of the slot 2 being substantially equal to the thickness constituted by the two wings folded up against each other.

The flexibility of the dressing enables it to follow the outline of the skin, including in the vicinity of the aneurysm zones that are associated with AVFs.

Once the operator has put the winged needle into place and the wings have folded down elastically into the deployed position over the top face of the dressing, the operator folds the dressing substantially along a transverse line T.

This transverse line is the line between the front first portion 3 and the rear second portion 5 of the dressing 1. This line may be scored, grooved, perforated, or of reduced thickness in the material forming the dressing.

In a variant, one edge of a transverse reinforcing strip may define this fold zone or line.

As shown in the figures, it should be observed that the rear portion 5 of the dressing is advantageously larger in area than the front portion 3, so as to cover it completely when the dressing is folded.

Figure 8:
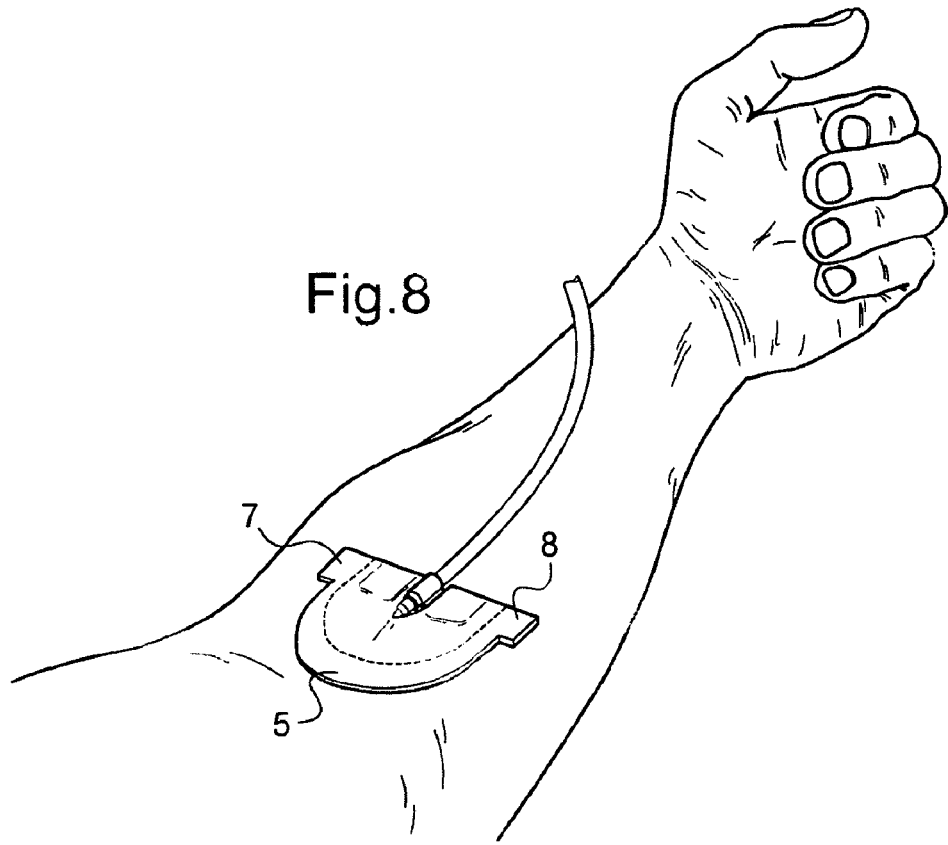
FIG. 8 is a view analogous to FIGS. 6 and 7, the winged needle being secured and protected in a dressing of the kind shown in FIGS. 1 and 2.

More precisely, once the dressing has been folded in half, the margin 6 and the lugs 7, 8 overlie the skin of the patient or the animal, as shown diagrammatically in FIG. 8.

Advantageously, the material constituting the lugs 7 and 8, and where appropriate the entire dressing 1, is stretchable at least in a longitudinal direction, and still more advantageously, in both the longitudinal direction and the transverse direction. The dressing is thus even more adaptable to the various curves of the patient's body.

It should be observed that the wings 11, 12 of the needle 10 are not themselves stuck to the skin, nor do they come into contact with an adhesive zone. Removal of the needle 10 is thus made more reliable than in prior art devices. It suffices merely to open the dressing 1 and deploy it around the transverse fold zone T, after which the needle 10 can be removed in conventional manner, the needle 10 then being passed through the slot 2, and finally the front bottom portion 4 of the dressing can be unstuck.

When the rear portion 5 of the dressing is folded down onto the front portion 3, the transverse fold zone of the dressing 1 forms an abutment for the wings 11, 12 of the needle 10.

In an embodiment that is not shown, the rear portion 5 is provided with a window in the form of a transparent film that faces a transparent film located in the front portion 3. This makes it possible to view the puncture site.

In an embodiment that is not shown, the rear portion 5 is also provided with a hole for passing an injection port of an injector device of the Cathlon® type, or cannulas made of PTFE, silicone, or polyurethane.

The invention claimed is:

1. A device for holding and protecting a needle or catheter, the device comprising a first portion and a second portion, each provided with an adhesive face covered in a detachable anti-adhesive sheet, the first portion being for securing to the skin in register with a penetration site selected for the needle or catheter, and the second portion being for covering the penetration site of the needle or catheter, wherein the device is made of a flexible material and further comprises a longitudinal slot for passing the needle or catheter and a transverse bearing zone for the needle on either side of the slot, only one face of the first portion being adhesive, the second portion being suitable and configured to be secured to the skin when overlying the penetration site of the needle, without being stuck to the first portion.

2. The device of claim 1, wherein the device is made of an elastic material.

3. The device of claim 1, further comprising a window of transparent or translucent material so as to enable the needle penetration point to be seen.

4. The device of claim 1, wherein the first and second portions constitute a single strip of flexible material hinged about a transverse fold zone.

5. The device of claim 4, wherein the longitudinal slot extends on either side of the fold zone, the maximum width of the slot as measured substantially along the fold direction being defined in said fold zone.

6. The device of claim 4, wherein the second portion is of shape substantially identical to the first portion, and is provided with lateral adhesive lugs.

7. The device of claim 6, wherein the lateral adhesive lugs are situated substantially in line with the fold zone.

8. The device of claim 6, wherein the second portion is of dimensions that are greater than those of the first portion and is provided with an adhesive peripheral margin.

9. The device of claim 4, further comprising a semirigid material on either side of the longitudinal slot, the thickness and the shape of the material enabling an angle of incidence for the needle to be substantially conserved.

10. The device of claim 1, wherein the second portion is provided with a hole for passing an injection port.

11. A perfusion kit comprising the device of claim 1 and a needle that is passed through the device and is temporarily secured thereto.

12. The kit of claim 11, wherein the needle is a winged needle and is temporarily secured to the device by snap-fastening.

13. A cover for securing and protecting an intravascular conduit, the cover comprising a sheet of material so thin and flexible as to permit application and retention on a skin surface, wherein:
 a first portion of the sheet comprises a top face that is non-adhesive and a bottom face that is so adhesive as to permit application and retention on a skin surface;
 a second portion of the sheet comprises a top face and a bottom face, wherein:
  the top face of the second portion is contiguous with the top face of the first portion;
  the top face of the second portion comprises a central region that is non-adhesive and a marginal region extending along a periphery of the central region, the central region being so sized and shaped as to cover the first portion when the second portion is folded over the first portion;
  the marginal region is so adhesive as to permit application and retention on a skin surface; and
  the bottom face of the second portion is non-adhesive and is contiguous with the bottom face of the first portion; and
 the sheet defines a slot extending longitudinally.

14. The cover of claim 13, wherein the top face of the first portion has the same size and shape as the central region of the top face of the second portion, so that the central region completely covers the top face of the first portion when the second portion is folded over the first portion.

15. The cover of claim 13, further comprising non-adhesive protective films removably adhered to the bottom face of the first portion and to the marginal region of the top face of the second portion.

16. A method of protecting an intravascular conduit and securing the conduit to a subject, the method comprising:
 inserting an end of the intravascular conduit through the subject's skin at a penetration site and into a vascular structure of the subject such that a retention feature of the conduit remains outside the subject's skin;
 positioning the cover of claim 13 so that the bottom face of the first portion adheres to skin adjacent the penetration site and so that a portion of the slot defined by the first portion of the sheet overlies the penetration site;
 positioning the retention feature of the conduit so that the retention feature overlies the top face of the first portion of the sheet;
 folding the sheet so that the second portion of the sheet covers the first portion of the sheet and also covers the retention feature, thereby protecting the conduit; and
 positioning the marginal region of the top face of the second portion of the sheet so that it adheres to the subject's skin, thereby securing the conduit to the subject's skin.

17. The method of claim 16, wherein the retention feature comprises foldable wings, and the step of positioning the retention feature comprises folding the wings against the first portion of the sheet.

18. The method of claim 16, wherein the vascular structure comprises at least one of an arteriovenous fistula, prosthesis, and graft.

19. The cover of claim 13, wherein a transverse line, along which the sheet material is scored, grooved, perforated, or has reduced thickness, delineates the sheet into the first portion and the second portion.

20. A cover for securing and protecting an intravascular conduit, the cover comprising a sheet of material so thin and flexible as to permit application and retention on a skin surface, wherein:
 a transverse line delineates the sheet into a first portion and a second portion such that the first portion and second portion are hinged about the transverse line;
 the first portion comprises a top face and a bottom face, the bottom face being so adhesive as to permit application and retention on a skin surface;
 the second portion comprises a top face and a bottom face, wherein:
  the top face of the second portion is contiguous with the top face of the first portion;
  the top face of the second portion comprises a central region and a marginal region extending along a periphery of the central region, the central region being so sized and shaped as to cover the first portion when the cover is folded over at the transverse line;

the marginal region is so adhesive as to permit application and retention on a skin surface; and the bottom face of the second portion is non-adhesive and is contiguous with the bottom face of the first portion; and the sheet defines a slot extending longitudinally along the sheet from the first portion, across the transverse line, and to the second portion.

21. The device of claim 1, wherein the second portion overlies the first portion when the device is applied.

22. The device of claim 1, wherein:

only one face of the second portion is adhesive;

the adhesive face of the first portion is on a bottom face;

the adhesive face of the second portion is on a top face; and the adhesive face of the second portion is sized, shaped, and positioned such that the second portion is not stuck to the first portion when the second portion is folded over the first portion and the anti-adhesive sheets are detached.

23. The cover of claim 20, wherein the sheet is scored, grooved, perforated or has reduced thickness along the transverse line.

24. The method of claim 16, wherein the marginal region of the top face of the second portion of the sheet is positioned such that it adheres to the subject's skin and does not adhere to the first portion of the sheet.

* * * * *